United States Patent [19]
Francese et al.

[11] Patent Number: 5,492,936
[45] Date of Patent: Feb. 20, 1996

[54] BIMODAL MOLECULAR WEIGHT HYALURONATE FORMULATIONS AND METHODS FOR USING SAME

[75] Inventors: James E. Francese, Anaheim; F. Richard Christ, Laguna Beach, both of Calif.

[73] Assignee: Allergan, Inc., Irvine, Calif.

[21] Appl. No.: 965,581

[22] Filed: Oct. 23, 1992

Related U.S. Application Data

[63] Continuation-in-part of Ser. No. 832,972, Feb. 10, 1992, which is a continuation-in-part of Ser. No. 621,290, Nov. 30, 1990, abandoned.

[51] Int. Cl.$^6$ .................... A61K 47/00; A61K 31/715
[52] U.S. Cl. ................ 514/772; 514/54; 514/912
[58] Field of Search ................ 514/54, 772, 912

[56] References Cited

U.S. PATENT DOCUMENTS

| | | |
|---|---|---|
| 4,141,973 | 1/1979 | Balazs . |
| 4,303,676 | 12/1981 | Balazs . |
| 4,517,295 | 5/1985 | Bracke et al. . |
| 4,784,990 | 11/1988 | Nimrod et al. . |

FOREIGN PATENT DOCUMENTS

| | | |
|---|---|---|
| 3080684 | 10/1986 | Australia . |
| 0138572 | 4/1985 | European Pat. Off. . |
| 0197718 | 10/1986 | European Pat. Off. . |
| 2478468 | 9/1981 | France . |
| WO8604355 | 7/1986 | WIPO . |
| WO9315744 | 8/1993 | WIPO . |

OTHER PUBLICATIONS

MartinDale 1960267 (1989).

Glasser et al, "Protective Effects of Viscous Solutions in Phacoemulsification and Traumatic Lens Implantation", Arch Ophthalmol—vol. 107, Jul. 1989.

Leith et al, "Comparison of the properties of AMVISC® and Healon®" J Cataract Refract Surg—vol. 13, Sep. 1987.

Patent Abstracts of Japan, vol. 13, No. 487, 1989.

Taverniti, Hyaluronate de sodium . . . , Bull. Mem. Soc. Fr. Ophthalmol., vol. 97, 1986, pp. 556–559.

Marchi, "Vantaggi derivanti . . . ", Ann. Ottalmol. Clin. Ocul., vol. 115, No. S, 1989, pp. 567–571.

Soll, et al, "Evaluation and Protection of Corneal Endothelium", AM Intra–Ocular Implant Soc J—vol. 6, Jul. 1980.

Pape et al, "The Use of Sodium Hyaluronate (Healon®) in Human Anterior Segment Surgery", Opthalmology, Jul. 1980 vol. 87, No. 7.

Anterior Segment Surgery with Use of a New Type of Sodium Hyaluronate Preparation IAL, Fruscella et al, 1987.

*Primary Examiner*—Zohreh Fay
*Attorney, Agent, or Firm*—Frank J. Uxa

[57] ABSTRACT

Compositions and methods useful for protecting human or animal eye cell layers and tissues exposed to trauma, e.g., during surgery, are disclosed. In one embodiment, the method comprises administering a protective amount of an ophthalmically acceptable aqueous composition containing a first alkali metal and/or alkaline earth metal hyaluronate fraction having a molecular weight of at least about 2 million, for example, in the range of about 2 million to about 4 million, and a second alkali metal and/or alkaline earth metal hyaluronate fraction having a molecular weight of about 200,000 to about 800,000, for example, in the range of about 300,000 to 700,000, to eye cell layers and tissues prior to the exposure to the trauma.

10 Claims, No Drawings

BIMODAL MOLECULAR WEIGHT HYALURONATE FORMULATIONS AND METHODS FOR USING SAME

RELATED APPLICATION

This application is a continuation-in-part of copending application Ser. No. 832,972, filed Feb. 10, 1992 now pending which, in turn, is a continuation-in-part of application Ser. No. 621,290 filed Nov. 30, 1990, now abandoned. The disclosure of each of these prior applications is incorporated in its entirety herein by reference.

BACKGROUND OF THE INVENTION

This invention relates to compositions and methods useful to protect human or animal eye cell layers and tissue subject to exposure to trauma. More particularly, the invention relates to compositions and methods involving hyaluronate fractions having differing molecular weights for protecting eye cell layers and tissues exposed to trauma, for example, during surgery.

When the natural lens of the eye becomes hazy or clouded, surgery is often indicated to remove the impaired lens. The current trend in such surgery is toward breaking the lens into a plurality of particles and then removing the particles, e.g., using the conventional phacoemulsification procedure. The use of a protective agent, in particular a viscoelastic fluid, that adheres to and protects the corneal endothelium during the surgical procedure is highly beneficial. Fluids containing high molecular weight range hyaluronates, that is hyaluronates having weight average molecular weights over 750,000, do not provide entirely acceptable adhesion to and/or protection of the corneal endothelium during certain surgical procedures. An example of such a fluid is that sold by Pharmacia Ophthalmics of Monrovia, Calif. under the trademark Healon®.

Formulations which include hyaluronic acid having a molecular weight of at least about 750,000, and preferably at least about 1,200,000 are disclosed in Balazs U.S. Pat. No. 4,141,973. Such formulations, which are not described in this patent as including any lower molecular weight hyaluronic acid, are disclosed as being useful in a number of applications, such as in the replacement of the aqueous humor after various intraocular surgical procedures, and as a biological prosthesis in the anterior chamber after cataract surgery.

Another formulation which includes high molecular weight hyaluronate (molecular weight of $1 \times 10^6$ to $4.5 \times 10^6$) is that disclosed in Balazs U.S. Pat. No. 4,303,672. The cosmetic formulations of this patent also include a low molecular weight hyaluronate fraction (molecular weight of 10,000 to 200,000) and protein in an amount ranging from 50% to 400% the weight of the hyaluronate. Such compositions are taught as having emollient, moisturizing, elasticizing and lubricating properties where applied to the skin. Such protein-containing hyaluronate compositions are not ophthalmically acceptable and would not be useful as protective agents in eye surgery.

Nimrod et al U.S. Pat. No. 4,784,990 discloses methods for producing cosmetic grade sodium hyaluronate containing between about 87% and 91% sodium hyaluronate of an average molecular weight between about 700,000 and 1,500,000 daltons, and clinical grade sodium hyaluronate with an average molecular weight of more than 700,000 daltons, usually in the range of from about 2 million to about 3 million daltons. The cosmetic grade of this material is not intended for use in the eye.

A sodium hyaluronate formulation, sold by Allergan, Inc. under the trademark Vitrax®, includes sodium hyaluronate having an average molecular weight of about 500,000 in a balanced salt aqueous solution. This formulation, which is useful in ophthalmic applications, does not contain a substantial amount of sodium hyaluronate having an average molecular weight in excess of about 1 million.

Bracke et al U.S. Pat. No. 4,517,295 discloses hyaluronic acid having an average molecular weight of about 55,000 which is produced from bacterial sources. Such hyaluronic acid is disclosed as having potentially significant use as an eye drop ingredient and as an ingredient of cosmetic formulations, as well as being useful in post-surgical applications for reducing complications due to fibrotic response and/or adhesion formation. This patent does not disclose the use of such hyaluronic acid as a protective agent in eye surgery.

Other formulations incorporate combinations of different materials, such as sodium hyaluronate and chondroitin sulfate. This type of product is described in Australian Patent 555,747. A product for use in providing protection during eye surgery and including sodium hyaluronate and chondroitin sulfate is that sold by Alcon Surgical, Inc. of Forth Worth, Tex. under the trademark Viscoat. Sources of chondroitin sulfate often include significant amounts of protein which need to be removed, using relatively complex and expensive separation techniques, before the purified chondroitin sulfate can be used in the eye.

There continues to be a need for compositions useful in protecting ocular or eye cell layers and tissues exposed to trauma, in particular trauma involved in ophthalmic surgical procedures.

SUMMARY OF THE INVENTION

New compositions and methods useful to protect human or animal ocular or eye cell layers and tissues subject to exposure to trauma have been discovered. The present ophthalmically acceptable compositions, which include two distinct molecular weight fractions of alkali metal and/or alkaline earth metal hyaluronates, have been found to provide a substantial degree of protection against trauma, such as that trauma which occurs during eye surgery, in particular eye surgery such as the removal of a diseased natural lens. The present compositions, which are based on two hyaluronate fractions having differing molecular weights, are relatively easy to place in the eye for use and maintain the space within the anterior or posterior chamber of the eye during surgery very well. In addition, these compositions are relatively easy to manufacture and to obtain governmental regulatory approval on, in comparison to compositions which include two or more significantly dissimilar adhesion/protective components.

It has unexpectedly been found that formulations which include both a high molecular weight range hyaluronate fraction, for example, having a weight average molecular weight of at least about 2 million, and a mid-range molecular weight hyaluronate fraction, for example, having a weight average molecular of about 200,000 to 700,000, have advantages of compositions containing either of these hyaluronate fractions alone. Further, and also unexpectedly, the present compositions reduce, or even minimize or eliminate, the problems which often occur or are present in compositions which contain only one of these hyaluronate fractions.

In one embodiment, the present ophthalmically acceptable compositions, preferably in the form of solutions, comprise water, a first alkali and/or alkaline earth metal hyaluronate fraction having a molecular weight of at least about 2 million and a second alkali and/or alkaline earth metal hyaluronate fraction having a molecular weight of about 200,000 to 700,000.

The first hyaluronate fraction preferably has a molecular weight in the range of about 2 million or about 3 million to about 4 million. The second hyaluronate fraction preferably has a molecular weight in the range of about 300,000 or about 400,000 to 700,000 or about 800,000. Preferably, the compositions are essentially non-pyrogenic and protein-free.

The ophthalmically acceptable compositions may, and preferably do, include at least one buffer component in an amount effective to control the pH of the composition and/or at least one tonicity adjuster component in an amount effective to control the osmolality of the composition. More preferably, the present compositions include both a buffer component and a tonicity adjuster component. The ophthalmically acceptable compositions of the present invention are preferably sterile.

In another embodiment of the present invention, methods to protect human or animal eye cell layers and tissues subject to exposure to trauma are provided. These methods comprise administering an amount effective to protect the ocular or eye cell layers and tissues of an ophthalmically acceptable composition, such as described herein, to the cell layers and tissues prior to exposure to trauma.

In a particularly useful embodiment, methods are provided for removing the natural lens from the eye of a human or animal. These lens removal methods comprise introducing a protective amount of an ophthalmically acceptable composition, such as described herein, into the eye of a human or animal. This introduced composition acts to adhere to and/or protect the eye cell layers and tissues, in particular the corneal endothelium, in proximity to the natural lens in the eye. The natural lens is caused to break into a plurality of particles, e.g., using a conventional surgical procedure which involves a potentially traumatic force associated with a relatively high degree of turbulence. These particles are removed from the eye. The hyaluronate-containing composition is also removed from the eye. In this manner, the defective natural lens, for example, a natural lens which has developed a cataract condition, is effectively removed from the eye without causing undue trauma or adverse effects to the eye cell layers and tissues in proximity to the natural lens which is removed. The presently useful compositions are relatively easy to administer to the eye, provide a very effective and high degree of protection against the potential trauma of the surgical procedure, and are relatively easy to remove, such as by irrigation/aspiration from the eye, after the protection is no longer needed. In particular, the present compositions are maintained in a protective amount on the eye cell layers and tissues in spite of the relative high degree of turbulence associated with causing the natural lens to break into a plurality of particles and/or removing the lens particles from the eye. Without such protection, lens fragments may impact and damage sensitive cell layers and tissues, such as the corneal endothelium.

DETAILED DESCRIPTION OF THE INVENTION

Ophthalmically acceptable compositions, in particular in the form of solutions, comprising water, a first alkali and/or alkaline earth metal hyaluronate fraction having a high molecular weight and a second alkali and/or alkaline earth metal hyaluronate fraction having a moderate or mid-range molecular weight, and preferably at least one buffer component and/or at least one tonicity adjuster component, have been found to provide substantial advantages, e.g., in terms of providing adhesion and/or protection to human or animal cell layers and tissues located in the eye which are exposed to trauma, in particular during surgical procedures. The present compositions also have other properties useful in viscoelastic fluids, such as high viscosity at zero shear, elasticity and pseudoplasticity.

The molecular weights noted herein are the weight average molecular weights of the fraction or fractions. This weight average molecular weight can be determined or measured by an indirect method, in particular the limiting viscosity method. The weight average molecular weight may be calculated from the limiting viscosity number by the published equation of Laurent et al, Fractionation of Hyaluronic Acid, Biochimica Et Biophysics Acta, 42, pps 476–485 (1960). Alternately, the weight average molecular weight can be determined using size exclusion chromatography techniques.

The first hyaluronate fractions useful in the present invention have high molecular weights, preferably molecular weights in the range of at least about 2 million and more preferably in the range of about 2 million or about 3 million to about 4 million.

The presently useful second hyaluronate fractions have molecular weights of about 200,000 to 700,000 or about 800,000, preferably in the range of about 300,000 or about 400,000 to 700,000 or about 800,000.

As is conventional and well known in the art, the first and second hyaluronate fractions can be obtained from various sources, such as rooster combs and other connective tissue, and from bacterial sources, in particular bacterial fermentation. The molecular weight fractions can be obtained using conventional separation procedures. Alternately, high molecular weight hyaluronates can be converted, for example, hydrolyzed, to moderate molecular weight hyaluronates, which are then recovered and used.

The first hyaluronate fraction and second hyaluronate fraction are each preferably independently selected from the group consisting of sodium hyaluronates, potassium hyaluronates, magnesium hyaluronates, calcium hyaluronates and mixtures thereof. More preferably, each of these fractions involves the same metal or metals. Sodium hyaluronate fractions are particularly useful.

The weight ratio of the first hyaluronate fraction to the second hyaluronate fraction in the presently useful compositions is preferably in the range of about 0.1 to about 4, more preferably about 0.2 to about 3. The concentration of the first hyaluronate fraction in the presently useful compositions is preferably in the range of about 1 mg/ml to about 50 mg/ml, more preferably about 2 mg/ml to about 10 mg/ml or about 20 mg/ml.

The present ophthalmically acceptable compositions are preferably essentially free of protein and essentially non-pyrogenic. The present compositions preferably include less than about 0.5% by weight of protein based on the total weight of first and second alkali and/or alkaline earth metal hyaluronates. More preferably, the present compositions have no detectable protein content and no detectable pyrogenicity.

The present compositions preferably include a major amount of liquid water, e.g., as a carrier or liquid medium for the hyaluronate fractions. The present ophthalmically acceptable compositions are preferably sterile, in particular prior to being used in the eye.

The present compositions preferably include at least one buffer component in an amount effective to control the pH of the composition and/or at least one tonicity adjuster component in an amount effective to control the osmolality of the composition. More preferably, the present compositions include both a buffer component and a tonicity adjuster component. Such components are useful in maintaining the present compositions ophthalmically acceptable so that, for example, the presence of these compositions in the eye do not result in any undue adverse effect or permanent damage to the eye. The use of one or more tonicity adjuster components is particularly important when the composition is to be applied to one or more portions of the cornea. Such tonicity adjuster components act to enhance the compatibility between the composition and the corneal tissue and/or to avoid damage to the corneal tissue. Such buffer components and tonicity adjuster components may be chosen from those which are conventional and well known in the art. Examples of useful buffer components include, but are not limited to, acetate buffers, citrate buffers, phosphate buffers, borate buffers and the like and mixtures thereof. Phosphate buffers are particularly useful. Useful tonicity adjuster components include, but are not limited to, salts, particularly sodium chloride, potassium chloride, any other suitable ophthalmically acceptable tonicity adjuster component and mixtures thereof. The amounts of buffer component and osmolality control component employed are preferably sufficient to maintain the pH of the compositions in the range of about 6 to about 8, more preferably about 7 to about 7.5, and the osmolality of the compositions in the range of about 200 to about 400, more preferably about 250 to about 350, mOsmol/kg, respectively.

The present compositions may include one or more other components in amounts effective to provide one or more useful properties and/or benefits to the present compositions.

The present compositions are useful in a method for protecting human or animal ocular or eye cell layers and tissues which are subject to being exposed to trauma, for example, during surgery. In one embodiment, the present method comprises administering a protective amount of such a composition to the ocular or eye-cell layers and tissues which are subject to exposure to trauma prior to exposure to the trauma. In this manner, such compositions preferably act to adhere to, or at least partially coat, the cell layers and tissues and/or provide protection for such cell layers and tissues from an imposed trauma.

The present compositions provide particularly good protection in situations where the trauma or potential trauma to which the eye cell layers or tissues is exposed occurs in a dynamic, turbulent environment, such as during a surgical procedure in which a natural lens to be removed is broken into particles, such as by using the conventional phacoemulsification technique.

A specific application in which the present compositions find significant usefulness is in a method for removing the natural lens, e.g., which is diseased, from the eye of a human or animal. In this embodiment, a protective amount of a composition in accordance with the present invention is introduced, such as by being injected, into the eye of a human or animal, for example, through an incision made in the eye. Such compositions can be relatively easily introduced into the eye, for example, using conventional injection cannulas or the like. The composition preferably adheres to at least a portion of the eye cell layers and tissues, in particular the corneal endothelium, in proximity to the natural lens to be removed. With the present composition in place, the natural lens is caused to break into a plurality of particles. One particularly useful approach to breaking up the natural lens is to use a conventional lens emulsification procedure, such as the well known phacoemulsification procedure. Unless the portions of the eye in proximity to the natural lens are provided with protection, the dynamic force used to break up the natural lens and/or the turbulence which often occurs during such lens removal procedures may also damage these other portions of the eye. The use of the present compositions has been found to provide adequate protection for these eye portions, in particular the corneal endothelium, against such potentially traumatic force and/or turbulence. The plurality of lens particles is removed, for example, using a conventional irrigation/aspiration procedure, from the eye. The present hyaluronate-containing composition is also removed, along with the lens particles and/or after further irrigation/aspiration, from the eye. Such removal occurs relatively easily and substantially without detrimentally affecting the remaining portions of the eye.

An intraocular lens can then be implanted in the eye, e.g., using a conventional technique, to replace the removed natural lens. After this implantation, the incision in the eye is closed, such as by suturing. The use of the present compositions, as described above, allows for effective removal of the natural lens from the eye without substantially damaging the eye cell layers and tissues in proximity to the natural lens.

The following non-limiting examples illustrate certain aspects of the present invention.

EXAMPLES 1 TO 3

Composition 1 was prepared by combining two separate buffered aqueous sodium hyaluronate-containing solutions. This composition included 5 mg/ml of a sodium hyaluronate fraction having a weight average molecular weight of about 3.5 million, and 15 mg/ml of a sodium hyaluronate fraction having a weight average molecular weight of about 500,000.

Composition 2 (comparative) was a balanced salt solution containing 30 mg/ml of a sodium hyaluronate fraction having a weight average molecular weight of about 500,000. Composition 2 is commercially available from Allergan, Inc., Irvine, Calif., and is sold under the trademark vitrax®. Composition 3 (comparative) was a phosphate buffered saline solution containing 10 mg/ml of a sodium hyaluronate fraction having a weight average molecular weight of about 3.5 million. Composition 3 is believed to be essentially equivalent to a composition which is commercially available from Pharmacia Ophthalmics, Monrovia, Calif., and is sold under the trademark Healon®.

Each of these compositions was tested by passing through a cannula. Composition 1 satisfactorily passed through a 27g cannula. Composition 2 was difficult to pass through a 25 g cannula. Composition 3 passed through a 27 g cannula very easily and readily. This test is indicative of the ability of a composition to be placed into an eye through a cannula. The results of this test, noted above, demonstrate that Composition 1 has sufficient flowability to be acceptable for placement into an eye through a cannula.

It was observed that Composition 1 handled much like Composition 3 in terms of cohesiveness and, thickness. These observations indicate that Composition 1 maintains the anterior or posterior chamber of the eye during surgery as well as Composition 3, which is known to be effective in performing this chamber maintaining function.

Each of the compositions was studied for coating effectiveness. The "surface" referred to below is on a slab of silicone polymer, such as conventionally used as an intraocular lens material. The results of these studies were as follows:

Composition 2

When a mass of this material was pushed with forceps along a surface, the material split into smaller masses, with some remaining stuck to the surface, thereby providing a coating layer. After being spread out on a surface, this material could not be gathered back together into a single mass and lifted off the surface. If the material which had been spread out on a surface was left for a period of time, it did regroup to some extent.

Composition 1

This material behaved much like Composition 2 except that, after being spread out on a surface, the material could, with some difficulty, be gathered up into a ball and lifted off the surface, although the material did have a degree of affinity for the surface.

Composition 3

A mass of this material could be rolled around like a little ball, and picked up and put back down as a unit without leaving a trail of material behind. This material was almost totally non-coating. When pushed with forceps, the material responded as a single mass sliding across the surface.

Each of the Compositions 1, 2 and 3 were tested in an enucleated rabbit eye during a phacoemulsification procedure and observations were recorded. Composition 1 remained in the eye during phacoemulsification much better than did Composition 3. However, it did not remain in the eye as well as did Composition 2.

These results and observations indicate that the coating and protecting abilities of Composition 1 are much closer to the coating and protecting abilities of Composition 2 than to the coating and protecting abilities of Composition 3. Thus, Composition 1 coats and protects the corneal endothelium during eye surgery very much like Composition 2 and very much better than Composition 3.

It should be noted that Composition 2 is known to have better coating and protecting abilities than Composition 3, while Composition 3 is very useful in maintaining the space within the anterior or posterior chamber during eye surgery.

Thus, quite unexpectedly, the present compositions, exemplified by Composition 1, have benefits of both compositions having only a mid-range molecular weight hyaluronate fraction (as exemplified by Composition 2) and compositions which have only a high molecular weight hyaluronate fraction (as exemplified by Composition 3). As noted above, the present compositions have very good flowability, for placement into the eye through a cannula; very effectively maintain the anterior or posterior chamber of the eye; and provide outstanding protection for the corneal endothelium during eye surgery. Neither Composition 2 nor Composition 3 provide this advantageous combination of benefits. Thus, the present compositions unexpectedly have increased utility and effectiveness, for example, in ocular surgery applications, relative to compositions which have only a mid-range molecular weight hyaluronate fraction or only a high molecular weight hyaluronate fraction.

The mid-range molecular weight hyaluronate fraction tested, that is having a weight average molecular weight of 500,000, is representative of hyaluronates having weight average molecular weights in the range of about 200,000 to 700,000 or about 800,000. That is, no substantial difference in composition performance would occur by changing the weight average molecular weight of the mid-range molecular weight hyaluronate fraction within the range about 200,000 to 700,000 or about 800,000. Similarly, no substantial difference in composition performance would occur by changing the weight average molecular weight of the high molecular weight hyaluronate fraction within the range of about 2 million to about 4 million or more.

While this invention has been described with respect to various specific examples and embodiments, it is to be understood that the invention is not limited thereto and that it can be variously practiced within the scope of the following claims.

What is claimed is:

1. A method for removing the natural lens from the eye of a human or animal which comprises:

introducing a protective amount of an ophthalmically acceptable aqueous composition into said eye of said human or animal, said ophthalmically acceptable aqueous composition comprising water, a first sodium hyaluronate fraction having a weight average molecular weight in the range of about 2 million to about 4 million, and a second sodium hyaluronate fraction having a weight average molecular weight in the range of about 400,000 to about 700,000, the weight ratio of said first sodium hyaluronate fraction to said second sodium hyaluronate fraction in said ophthalmically acceptable aqueous composition is in the range of about 0.1 to about 4, said ophthalmically acceptable aqueous composition adhering to at least one portion of the eye in proximity to said natural lens in said eye, said introducing step being more easily conducted relative to a similar introducing step employing a similar ophthalmically acceptable aqueous composition containing none of said first sodium hyaluronate fraction;

causing said natural lens to break into a plurality of particles, said composition being more effective in protecting said eye of said human or animal during said causing step relative to a similar ophthalmically acceptable aqueous composition containing none of said second sodium hyaluronate fraction;

removing said plurality of particles; and removing said ophthalmically acceptable aqueous composition from said eye.

2. The method of claim 1 wherein said ophthalmically acceptable aqueous composition further includes at least one buffer component in an amount effective to control the pH of said ophthalmically-acceptable aqueous composition and at least one tonicity adjuster component in an amount effective to control the osmolality of said ophthalmically acceptable aqueous composition.

3. The method of claim 2 wherein said ophthalmically acceptable aqueous composition has a pH in the range of about 7 to about 7.5, and an osmolality in the range of about 250 to about 350 mOsmol/kg, and said first metal hyaluronate fraction has a weight average molecular weight in the range of about 3 million to about 4 million.

4. The method of claim 1 wherein said ophthalmically acceptable aqueous composition has a pH in the range of about 6 to about 8.

5. The composition of claim 1 wherein the weight ratio of said first sodium hyaluronate fraction to said second sodium hyaluronate fraction in said ophthalmically acceptable aqueous composition is in the range of about 0.25 to about 4.

6. The composition of claim 1 wherein the weight ratio of said sodium metal hyaluronate fraction to said second sodium hyaluronate fraction in said ophthalmically acceptable aqueous composition is in the range of about 0.2 to about 3.

7. The composition of claim 1 wherein said first sodium hyaluronate fraction is present in said ophthalmically acceptable aqueous composition in a concentration in the range of about 2 mg/ml to about 20 mg/ml.

8. The method of claim 1 wherein said ophthalmically acceptable aqueous composition is introduced into at least one of the anterior chamber or the posterior chamber of said eye of said human or animal and is substantially as effective in maintaining the anterior chamber or posterior chamber of said eye of said human or animal relative to a similar ophthalmically acceptable aqueous composition containing none of said second sodium hyaluronate fraction.

9. The method of claim 1 wherein said ophthalmically acceptable aqueous composition has a pH in the range of about 7 to about 7.5 and an osmolality in the range of about 250 to about 350 mOsmol/kg, said first metal hyaluronate fraction has a weight average molecular weight in the range of about 3 million to about 4 million, the weight ratio of said first sodium hyaluronate fraction to said second sodium hyaluronate fraction in said ophthalmically acceptable aqueous composition is in the range of about 0.2 to about 3, and said first sodium hyaluronate fraction is present in said ophthalmically acceptable aqueous composition is a concentration in the range of about 2 mg/ml to about 20 mg/ml.

10. The method of claim 8 wherein said ophthalmically acceptable aqueous composition has a pH in the range of about 7 to about 7.5 and an osmolality in the range of about 250 to about 350 mOsmol/kg, said first metal hyaluronate fraction has a weight average molecular weight in the range of about 3 million to about 4 million, the weight ratio of said first sodium hyaluronate fraction to said second sodium hyaluronate fraction in said ophthalmically acceptable aqueous composition is in the range of about 0.2 to about 3, and said first sodium hyaluronate fraction is present in said ophthalmically acceptable aqueous composition is a concentration in the range of about 2 mg/ml to about 20 mg/ml.

* * * * *